(12) United States Patent
Olsen

(10) Patent No.: US 10,067,263 B2
(45) Date of Patent: Sep. 4, 2018

(54) BIOFOULING TARGET REMOVAL

(71) Applicant: PGS Geophysical AS, Oslo (NO)

(72) Inventor: Sverre Olsen, Lommedalen (NO)

(73) Assignee: PGS Geophysical AS, Oslo (NO)

( * ) Notice: Subject to any disclaimer, the term of this patent is extended or adjusted under 35 U.S.C. 154(b) by 139 days.

(21) Appl. No.: 15/160,029

(22) Filed: May 20, 2016

(65) Prior Publication Data

US 2017/0059741 A1    Mar. 2, 2017

Related U.S. Application Data

(60) Provisional application No. 62/210,228, filed on Aug. 26, 2015.

(51) Int. Cl.
| | |
|---|---|
| *G01V 13/00* | (2006.01) |
| *G01V 1/20* | (2006.01) |
| *G01V 1/38* | (2006.01) |
| *G01N 21/94* | (2006.01) |
| *H04N 5/225* | (2006.01) |
| *B08B 7/00* | (2006.01) |
| *G02B 27/00* | (2006.01) |
| *B63B 59/06* | (2006.01) |
| *B63C 11/00* | (2006.01) |

(52) U.S. Cl.
CPC ............ *G01V 13/00* (2013.01); *B08B 7/0042* (2013.01); *G01N 21/94* (2013.01); *G01V 1/201* (2013.01); *G01V 1/38* (2013.01); *G02B 27/0006* (2013.01); *H04N 5/2256* (2013.01); *B63B 59/06* (2013.01); *B63C 11/00* (2013.01); *G01N 2201/06113* (2013.01)

(58) Field of Classification Search
None
See application file for complete search history.

(56) References Cited

U.S. PATENT DOCUMENTS

| | | | |
|---|---|---|---|
| 7,496,228 B2 | 2/2009 | Landwehr et al. | |
| 9,072,281 B2 | 7/2015 | Beck | |
| 2003/0060810 A1 | 3/2003 | Syrowicz et al. | |
| 2012/0050520 A1 | 3/2012 | Thoren et al. | |
| 2012/0266803 A1* | 10/2012 | Zediker | B63G 8/001 |
| | | | 114/337 |
| 2013/0265850 A1* | 10/2013 | Wu | B08B 1/008 |
| | | | 367/20 |
| 2014/0069313 A1 | 3/2014 | Nielsen et al. | |
| 2014/0083449 A1 | 3/2014 | Erneland | |
| 2015/0075066 A1* | 3/2015 | Stowe | A01D 34/015 |
| | | | 47/1.3 |

FOREIGN PATENT DOCUMENTS

| | | |
|---|---|---|
| CN | 102700692 A | 10/2012 |
| WO | 2016096770 A1 | 6/2016 |

OTHER PUBLICATIONS

European Search Report for Application No. 16184780.1 dated Jan. 13, 2017.
Lasers in the Conservation of Art, Proceedings of the International Conference Lacona VII, Sep. 17-21, 2007, p. 4.

* cited by examiner

*Primary Examiner* — Eileen M Adams
(74) *Attorney, Agent, or Firm* — Patterson + Sheridan, LLP

(57) ABSTRACT

Certain aspects of the present disclosure generally relate to cleaning geophysical equipment in water. An exemplary method includes illuminating, with laser light, an obstruction on the geophysical equipment while the geophysical equipment is deployed in an operable configuration (e.g., towed by a survey vessel).

21 Claims, 6 Drawing Sheets

BIOFOULING TARGET REMOVAL

CROSS-REFERENCE TO RELATED APPLICATIONS

The present Application for Patent claims priority to U.S. Provisional Application No. 62/210,228, filed Aug. 26, 2015, which is assigned to the assignee of the present application and hereby expressly incorporated by reference herein in its entirety.

BACKGROUND

Field of the Disclosure

Certain aspects of the present disclosure generally relate to removing fouling entities from marine equipment, and, more particularly, to laser-removal of barnacle larvae and barnacles from sensor streamers.

Description of Related Art

Marine seismic surveys are one type of marine geophysical survey which utilizes sound waves transmitted to the earth's crust and reflected back to recording sensors. The recording sensors may be hydrophones or other sensors in one of a number of towing assemblies, commonly called streamers or sensor streamers, that may be towed behind a survey boat. When towed behind the survey boat, the streamers may be submerged. A sound, or other energy, source may also be towed in the water behind the survey boat for transmitting energy to be received by the receivers of the streamers. One common application of marine geophysical surveying is oil and gas exploration in marine environments. More particularly, sound waves received during a marine seismic survey may be analyzed to locate hydrocarbon bearing geological structures, and thus determine where deposits of oil and natural gas may be located. In a similar fashion, marine electromagnetic (EM) surveys may be conducted using EM energy transmitted by a submerged source and detected by EM receivers.

Periodically, cleaning operations may be conducted on streamers used in marine seismic surveys. Cleaning operations may be conducted by a crew on a workboat separate from the survey boat. To clean a particular one of the towed streamers, the workboat crew may lift the streamer out of the water, clean by hand, and lower the streamer back into the water. Since the streamers can have significant length, (e.g., 8 km), in some cases only a portion of the streamer is lifted out of the water. The workboat crew may progressively lift portions of a particular streamer out of the water until cleaning is complete. The workboat crew may then progress to the next streamer and repeat the process. The process may be subsequently repeated until all streamers have been cleaned. The process of cleaning using a workboat crew can be very time consuming, and in some cases, dangerous to the crew members that perform the work.

Remotely operated vehicles (ROVs) may be useful for supporting marine geophysical surveying. For example, an ROV may be deployed to maintain (e.g., clean, repair) a streamer towed behind a survey boat, allowing maintenance of a streamer without reeling the streamer back onto the survey boat. ROVs may also be used for other tasks in marine exploration, such as placing equipment on the seabed.

Lifting a streamer out of the water may prevent the streamer from collecting survey data, thus interfering with survey operations. Cleaning operations may also be conducted on streamers with a streamer cleaning unit (SCU) that cleans a streamer while it is submerged. A streamer cleaning unit may be attached to a streamer and clean the streamer with brushes and other tools to physically remove obstructions from the streamer. The use of brushes and other tools on the streamers produces sounds or other noise that can interfere with collecting survey data. Similarly, the presence of metal parts of an SCU in close proximity to a streamer may interfere with collection of EM survey data. It is therefore desirable to clean streamers by methods that produce less sound interference and EM interference to improve the collection of survey data.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

DETAILED DESCRIPTION

According to embodiments of the present disclosure, techniques are provided to clean submerged geophysical equipment using laser light. The laser light may be transmitted by one or more lasers. The provided techniques include methods, apparatus, and systems for cleaning obstructions from geophysical equipment. Such obstructions may include barnacle larvae and barnacles. In some embodiments of the present disclosure, the geophysical equipment may be a sensor streamer that may be towed behind a survey vessel.

In at least one embodiment, a cleaning apparatus may include one or more lasers operable to emit laser light directed at a streamer and/or an obstruction on a streamer. The lasers may be periodically activated, activated in response to a command by a user at a control interface, activated in response to detection of an obstruction on the streamer, or activated continuously.

It is to be understood the present disclosure is not limited to particular devices or methods, which may, of course, vary. This disclosure may be embodied in many different forms and should not be construed as limited to any specific structure or function presented. In particular, while aspects of the disclosure are described in terms of a laser producing light in the green portion of the visible light spectrum, e.g., with wavelengths between 480 nm and 540 nm, the disclosure is not so limited.

It is also to be understood that the terminology used herein is for the purpose of describing particular embodiments only, and is not intended to be limiting. As used herein, the singular forms "a", "an", and "the" include singular and plural referents unless the context clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

The word "exemplary" is used herein to mean "serving as an example, instance, or illustration." Any aspect described herein as "exemplary" is not necessarily to be construed as preferred or advantageous over other aspects.

Figure 1:
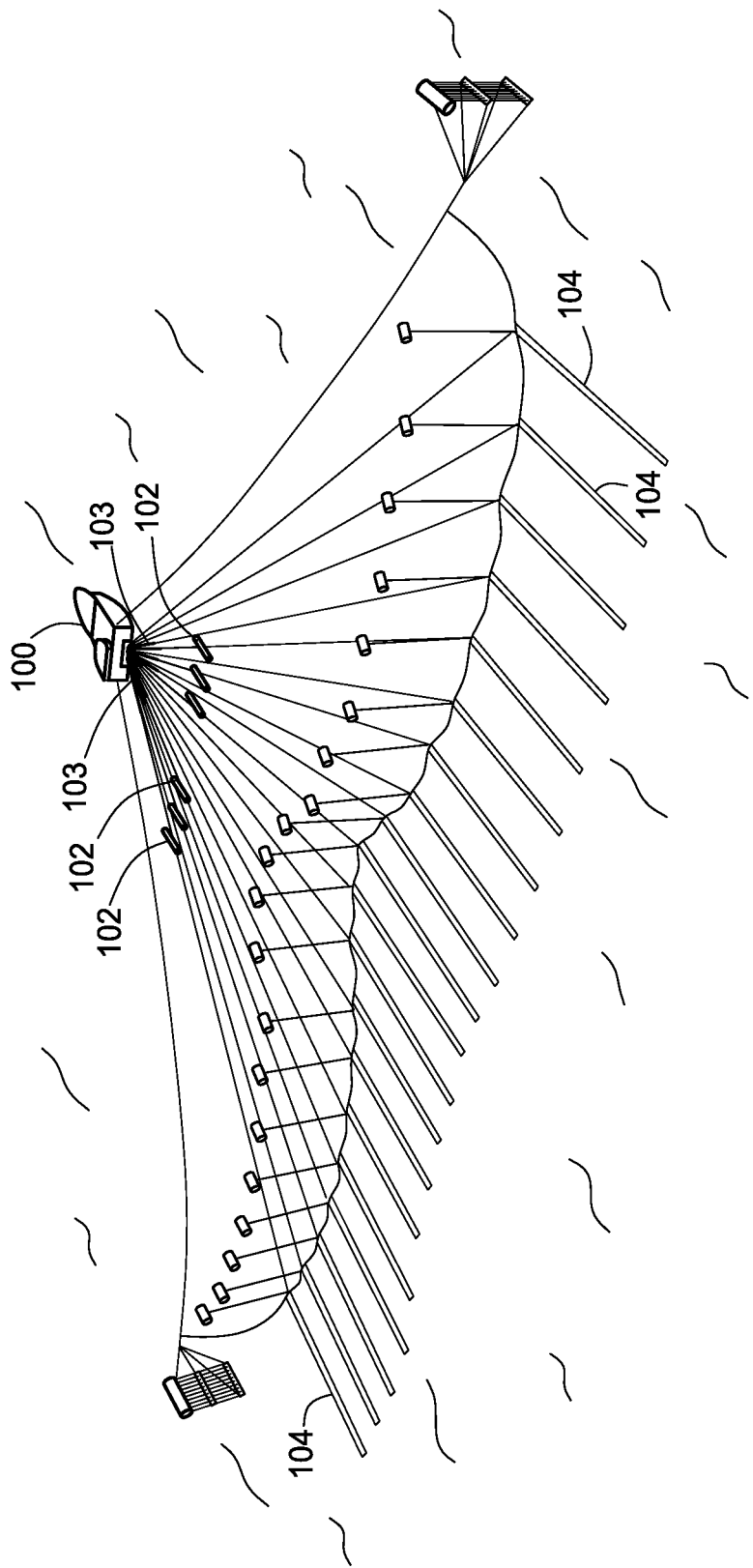
FIG. 1 illustrates an exemplary survey vessel towing an array of submerged streamers operating according to previously known techniques.

FIG. 1 illustrates an exemplary survey vessel 100 towing an array of submerged streamers 104. Each of the submerged streamers 104 may include a number of seismic sensors, EM receivers, or a combination thereof. The types of sensors that may be implemented in a given streamer 104 include (but are not limited to) hydrophones, geophones, electrodes, and magnetometers. Moreover, a given streamer 104 may include more than one type of sensor (e.g., a combination of hydrophones, geophones, electrodes, and magnetometers). Various operational considerations may make certain streamer towing depths advantageous. In some embodiments, single sensor streamers 104 may be towed at depths between about 4 meters and 30 meters. In some embodiments, dual sensor streamers may be towed at depths between 15 and 30 meters.

Survey vessel 100 may also tow a number of sources 102 via tow cables 103. In some embodiments, sources 102 may be towed by another vessel (not shown). Sources 102 may include a variety of seismic sources, such as marine vibrators or air guns. Sources 102 may also include a variety of electromagnetic (EM) sources, such as antennas or magnetic coils. In some embodiments, sources 102 may transmit sound waves into the water, the echoes of which may be detected by the seismic sensors of the streamers 104. In some embodiments, sources 102 may transmit EM signals into the water, which may be detected by the EM receivers of the streamers 104. The sensors of streamers 104 may be electrically coupled to electronic equipment aboard survey vessel 100 that may be used to analyze geophysical data, such as received echoes or detected energy. Using the arrangement shown in FIG. 1, marine geophysical surveys may be conducted. Among the uses of information obtained from such surveys may be the identification of geological formations indicative of oil and/or natural gas deposits.

During the conduct of marine geophysical surveys, equipment may at times become obstructed. For example, the growth of barnacles and barnacle larvae on streamers may occur during the conduct of marine geophysical surveys, particularly in certain geographic locations. In colder locations, ice may sometimes form on geophysical survey equipment such as the streamers discussed herein. When obstructions such as barnacles are attached to the streamers, the sensitivity of the sensors contained in the streamers may be reduced. This in turn can adversely affect the data collected in the survey. Accordingly, cleaning of the streamers may be periodically performed in order to remove obstructions from the streamers 104 and thus to increase the quality of a survey in progress.

In some embodiments, the cleaning of the streamers (and more generally, of geophysical equipment) may include illuminating obstructions, sensors, and/or the streamers with light from one or more lasers. The light from the lasers may be transmitted toward the geophysical equipment undergoing the cleaning operations. Illuminating obstructions with laser light may be effective in loosening or removing various obstructions that may otherwise adhere to the geophysical equipment. Laser light at in the green portion of the visible light spectrum (e.g., at wavelengths of 480 nm to 540 nm) may be especially effective at removing obstructions from geophysical equipment. Such obstructions that may be loosened or removed using laser light may include, but are not limited to, barnacle larvae, barnacles, and biological film. In cases where the obstructions are not completely removed, additional cleaning using brushes and/or other types of cleaning apparatuses may be utilized to complete the cleaning.

Figure 2:
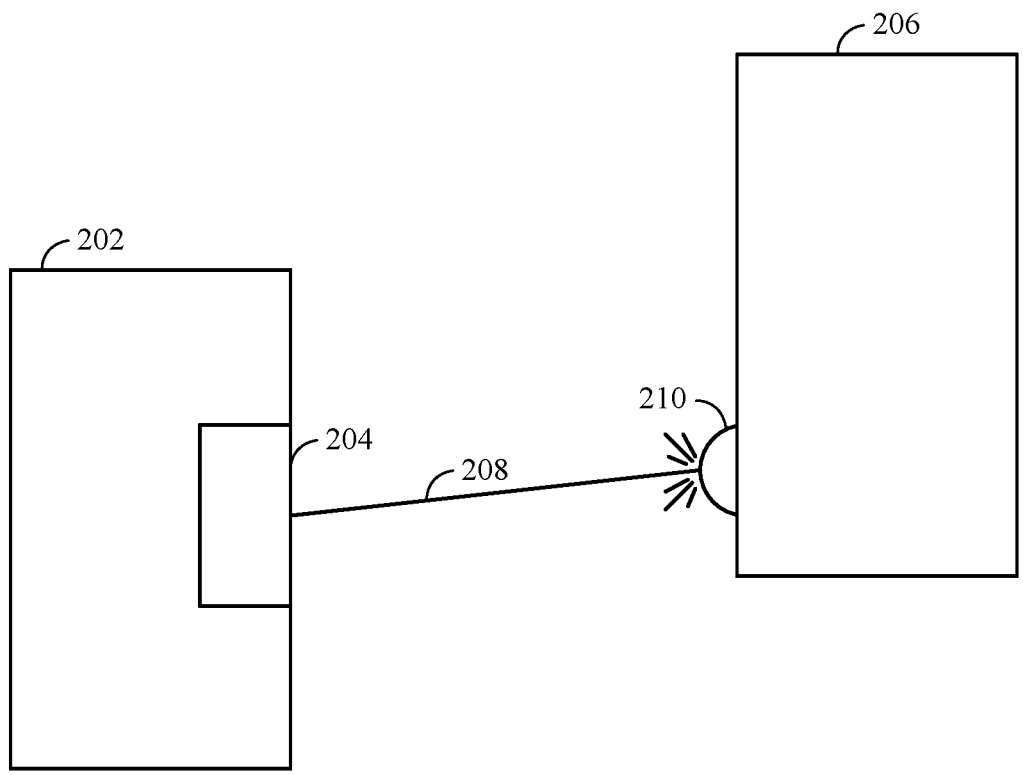
FIG. 2 illustrates one embodiment of a cleaning apparatus, according to aspects of the present disclosure.

FIG. 2 is a diagram illustrating one embodiment of a cleaning apparatus conducting a cleaning of a piece of geophysical equipment using laser light. In the embodiment shown, cleaning apparatus 202 includes one or more laser sources 204 that are configured to emit laser light. As used herein, the term laser source refers to any type of laser capable of transmitting laser light and mechanisms for aiming the laser light. Such a laser may include (but is not limited to) gas lasers, diode lasers, and solid-state lasers. Light from the laser may be aimed by means of an optical waveguide (e.g., an optical fiber) and/or lenses. The laser light 208 may be transmitted directly toward geophysical equipment 206. In particular, the laser light may be aimed at an obstruction 210. The laser light may loosen or remove obstructions adhering to external surfaces of geophysical equipment 206. In particular, barnacles, barnacle larvae, and biological film may be removed by heating caused by illuminating the barnacles, barnacle larvae, and biological film with laser light.

Cleaning of equipment (e.g., streamers 104, sources 102, or tow cables 103 shown in FIG. 1) may be facilitated by use of a cleaning vessel, such as a remotely operated vehicle (ROV). As will be described in more detail below, an ROV may operate a laser source to clean survey equipment and/or deliver a streamer cleaning unit (SCU) to the vicinity of a streamer and/or attach an SCU to a streamer.

Figure 3:
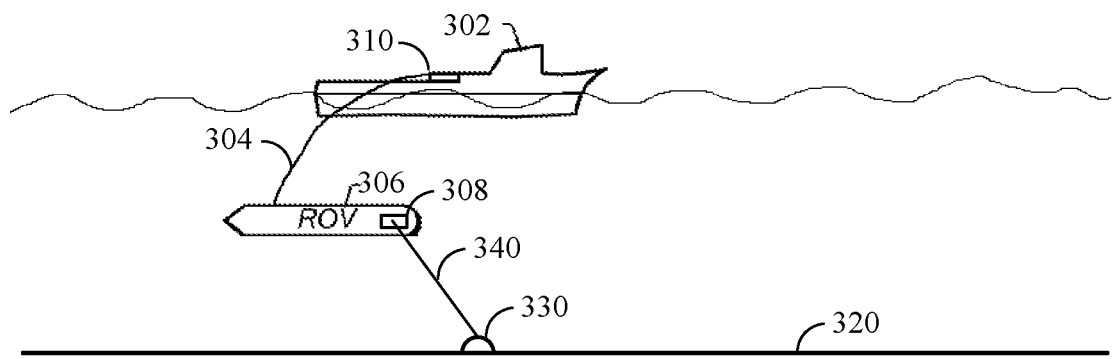
FIG. 3 illustrates a chase vessel with an ROV operating according to aspects of the present disclosure.

FIG. 3 illustrates an exemplary deployment vessel 302 (e.g., a chase vessel) with an exemplary cleaning vessel 306 (e.g., an ROV) operating according to aspects of the present disclosure. Deployment vessel 302 may be a vessel separate from a survey vessel (e.g. survey vessel 100 in FIG. 1). The deployment vessel 302 may also be referred to as a mother vessel to cleaning vessel 306. In the embodiment shown, the cleaning vessel 306 is controlled from the deployment vessel 302. In embodiments, the cleaning vessel 306 can be an autonomous unit. For example, vessel 306 can be controlled by controllers located on cleaning vessel 306 such that cleaning vessel 306 is not tethered to deployment vessel 302. The illustrated exemplary cleaning vessel 306 is tethered to the deployment vessel 302 by a tether 304, which may be a group of cables. Signals may be exchanged between a control station 310, which may be control consoles, displays, and/or computers, aboard the deployment vessel 302 and the cleaning vessel 306 via the tether. The signals may comprise commands from the deployment vessel 302 and data (e.g., video signals) from the cleaning vessel 306. One or more operators may direct the maneuvering and other operations of the cleaning vessel 306 using the control station 310, which generates commands sent to the cleaning vessel 306 via the tether 304.

An exemplary streamer 320 is also illustrated in FIG. 3. Streamer 320 may be similar to the streamers 104 illustrated in FIG. 1. Streamer 320 may also be an example of geophysical equipment illustrated in FIG. 2. The exemplary streamer is illustrated with an exemplary obstruction 330 attached. The exemplary obstruction may be a barnacle or barnacle larva.

According to aspects of the present disclosure, cleaning vessel 306 may comprise a laser source 308. The laser source 308 of the cleaning vessel 306 may direct a field of laser light 340 toward the obstruction 330 to illuminate the obstruction with the laser light and thus loosen or remove the obstruction from the streamer 320. Laser light may remove or loosen the obstruction by melting or vaporizing the obstruction or a portion of the obstruction. In the case of an obstruction comprising a biological organism (e.g., a barnacle, a barnacle larva), the laser light may interfere with the biological organism's ability to adhere to the streamer.

Cleaning vessel 306 may also comprise a video camera, sonar devices, and/or other sensors for gathering information regarding conditions in the vicinity of the cleaning vessel 306. In particular, the sensors of the cleaning vessel 306 may gather information regarding a streamer and obstructions on the streamer. One or more video cameras and a computer system programmed to perform optical recognition may be included on the cleaning vessel 306 and may determine the presence of obstructions on the streamer. The computer system may also control the laser source 308 and cause the laser source 308 to illuminate (e.g., with continuous beams or pulses) the obstructions on the streamer. That is, the computer system may comprise software to analyze imagery supplied by the video cameras to recognize and locate one or more obstructions on a streamer. The computer system may recognize and locate an obstruction using the software and then control (e.g., using other software) the laser source 308 to illuminate the recognized and located obstruction. The computer system may be in the control unit 310 and/or on board the cleaning vessel 306.

In some embodiments of the present disclosure, a computer system may cause a laser on the cleaning vessel 306 to illuminate the streamer. That is, in some embodiments, a computer system (e.g., on the cleaning vessel 306 and/or in the control unit 310) may control a laser source 308 in the cleaning vessel 306 to illuminate (e.g., with a fanned beam or multiple pulses of a narrow beam) all or a portion of a streamer, rather than illuminating only obstructions on the streamer.

In some embodiments of the present disclosure, an ROV may be used to facilitate cleaning of a streamer by carrying a streamer cleaning unit (SCU) to the vicinity of the streamer, wherein the SCU includes one or more lasers configured to illuminate obstructions on one or more streamers. An SCU may include one or more video cameras and a computer system programmed to perform optical recognition to determine the presence of obstructions on the streamer. The computer system may also control the laser and cause the laser to illuminate the obstructions on the streamer.

Figure 4:
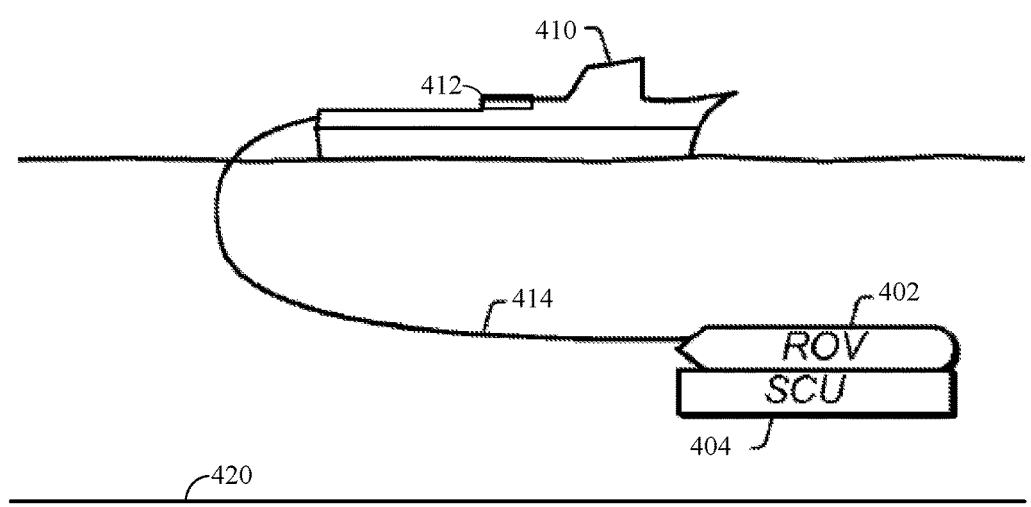
FIG. 4 illustrates an exemplary ROV and an exemplary SCU operating according to aspects of the present disclosure.

FIG. 4 is a diagram illustrating an exemplary cleaning vessel 402 (e.g., an ROV) and an attached exemplary SCU 404 approaching a submerged streamer 420, which may be deployed in an operational configuration (e.g., being towed behind a survey vessel, such as survey vessel 100 shown in FIG. 1). In FIG. 4, an SCU 404 has been attached to cleaning vessel 402. Cleaning vessel 402 may be similar to cleaning vessel 306 illustrated in FIG. 3. The attachment of the cleaning vessel 402 to the SCU 404 may occur either with at least one of the cleaning vessel 402 and the SCU 404 above the waterline or with both submerged in the water. The cleaning vessel 402 may be controlled by an operator at control unit 412 aboard the deployment vessel 410. Commands from the control unit 412 may be conveyed to the cleaning vessel 402 via the tether 414. The operator may direct the cleaning vessel 402, with the SCU 404 attached thereto, to maneuver to a streamer 420 to be cleaned while the streamer 420 is submerged and deployed in an operational configuration. The exemplary SCU 404 shown includes one or more laser sources, one or more video cameras, and a computing system.

Figure 5:
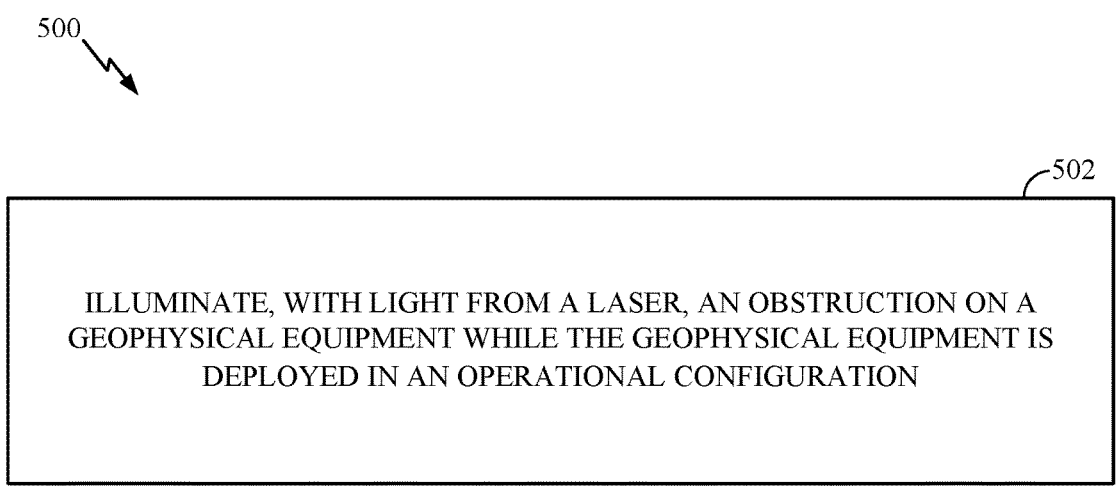
FIG. 5 sets forth an exemplary operation for cleaning geophysical equipment, according to aspects of the present disclosure.

FIG. 5 sets forth an operation 500 for cleaning (e.g., removing obstructions from) geophysical equipment (e.g., a sensor streamer), according to aspects of the present disclosure. The operation 500 may be performed by an adapter, a cleaning vessel (e.g., cleaning vessel 306 shown in FIG. 3), an ROV, or an adapter attached to an ROV or a cleaning vessel.

The operation 500 comprises block 502, wherein an adapter, SCU, ROV, cleaning vessel, or cleaning tool illuminates, with light from a laser, an obstruction on a geophysical equipment while the geophysical equipment is deployed in an operational configuration, (e.g., while being used to gather survey data) in a body of water. As previously described, the geophysical equipment may remain submerged in the body of water while a laser is used to clean (e.g., remove or loosen) obstructions on the geophysical equipment. Also as previously described, the laser may be coupled with a cleaning vessel (e.g., mounted on an ROV or mounted on a tool coupled to an ROV). The geophysical equipment may be a sensor streamer, and the laser may be coupled with a cleaning vessel and may illuminate one or more obstructions on the streamer while the cleaning vessel traverses a length of the sensor streamer. Also as previously described, the laser may illuminate the sensor streamer in addition to illuminating the obstruction. Instead of being coupled with an ROV, the laser may be coupled with an adapter (e.g., an SCU) that is coupled with the geophysical equipment. When the geophysical equipment is a sensor streamer, the method may further include coupling the adapter to the sensor streamer and illuminating the obstruction while the adapter traverses a length of the sensor streamer.

Figure 6:
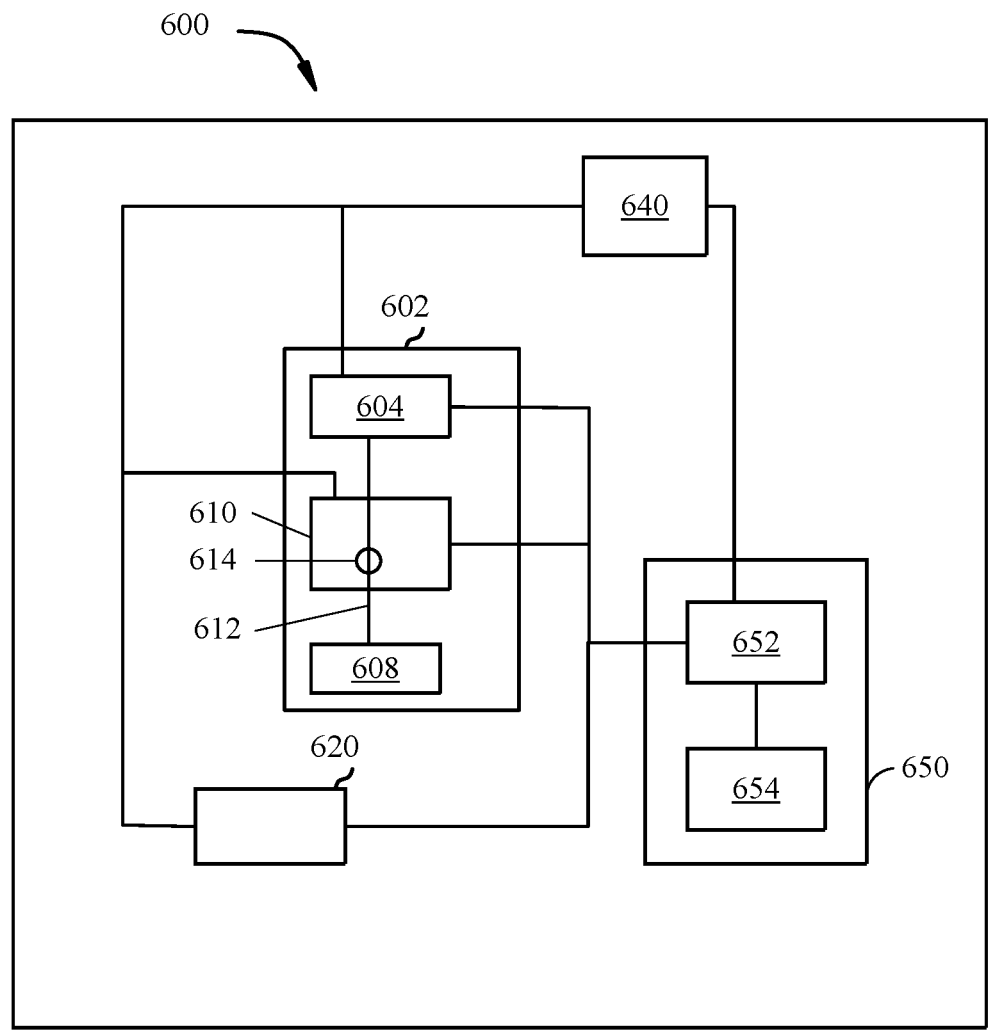
FIG. 6 illustrates a block diagram of an exemplary system in which aspects of the present disclosure may be practiced

FIG. 6 illustrates a block diagram of an exemplary system 600 in which aspects of the present disclosure may be practiced. The system 600 may be included in an adapter or a cleaning vessel (e.g., cleaning vessel 306 shown in FIG. 3). The system 600 includes a laser source 602, a video camera 620, a power supply 640, and a computing subsystem 650.

The laser source 602 includes a laser 604, a laser-aiming mechanism 610, and a window 608. The laser 604 may be a semiconductor laser, a fiber laser, or another type of laser capable of generating laser light (e.g., laser light in the green portion of the visible light spectrum). The laser 604 generates a beam of laser light for cleaning obstructions from geophysical equipment (e.g., sensor streamers), as previously described. The laser-aiming mechanism 610 may comprise a fiber-optic cable 612 attached to a gimbal 614. The gimbal 614 is controlled to direct one end of the fiber-optic cable 612 at the window 608, while a second end of the fiber-optic 612 cable is coupled with the laser 604 to collect laser light generated by the laser 604. The laser-aiming mechanism 610 directs beams of laser light from the laser 604 out the window 608 and toward geophysical equipment to be cleaned. In some embodiments of the present disclosure, the power rating of the laser 604 is in the range of five to twenty watts (e.g., eight watts), and the laser source 602 directs beams of laser light that are one to two millimeters in diameter.

The video camera 620 is aimed at the region that the window 608 is aimed toward. In some embodiments, the video camera 620 is aimed through the window 608, although this is not required and the video camera 620 may be aimed through a separate window. The video camera 620 gathers imagery of geophysical equipment to be cleaned and of the areas illuminated by the laser light.

The power supply 640 may be a battery or a connection to another vessel, such as a cable to a chase vessel. The power supply 640 supplies electric power to the laser source 602, video camera 620, and computing subsystem 650.

The computing subsystem 650 controls the operation of the laser source 602 and video camera 620. The computing subsystem 650 may identify and locate geophysical equipment (e.g., streamers) and obstructions on the geophysical equipment based on imagery supplied from the video camera 620. The computing subsystem 650 directs the laser source 602 in illuminating the geophysical equipment and/or obstructions with laser light. The computing subsystem 650 may comprise one or more processors (e.g., CPUs) 652 and a memory 654. The memory 654 may store program instructions for operation of the system 600, and the processors 652 may execute the program instructions.

Aspects of the present disclosure can include methods, apparatus, and systems for cleaning geophysical equipment using laser light, as described above. The geophysical equipment may be submerged in a body of water while being cleaned, also as described above.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Various advantages of the present disclosure have been described herein, but embodiments may provide some, all, or none of such advantages, or may provide other advantages.

What is claimed is:

1. A method for cleaning geophysical equipment, comprising:
    illuminating, with light from a laser, an obstruction on a marine geophysical equipment while the marine geophysical equipment is deployed in an operational configuration, wherein the laser is coupled to an adapter that is removably attached to an underwater vehicle, the adapter having an exit aperture for the laser that faces the marine geophysical equipment.

2. The method of claim 1, wherein the laser is coupled with a cleaning vessel.

3. The method of claim 2, wherein the cleaning vessel is a remotely operated vehicle.

4. The method of claim 2, wherein the marine geophysical equipment comprises a sensor streamer, the operational configuration comprises the sensor streamer being towed behind a survey vessel, and the obstruction is coupled to the sensor streamer, and wherein the method further comprises:
    the illuminating occurs during a period of time while the cleaning vessel traverses a length of the sensor streamer.

5. The method of claim 2, wherein the marine geophysical equipment comprises a sensor streamer and the obstruction is coupled to the sensor streamer, and wherein the method further comprises:
    illuminating a portion of the sensor streamer while the cleaning vessel traverses a length of the sensor streamer.

6. The method of claim 1, wherein the marine geophysical equipment comprises a sensor streamer, and wherein the laser is coupled with a streamer cleaning unit that is coupled with a remotely operated vehicle.

7. The method of claim 1, further comprising:
    locating the obstruction with a camera.

8. An apparatus for cleaning geophysical equipment, comprising:
    an underwater vehicle; and
    a laser operable to illuminate an obstruction on a marine geophysical equipment deployed in an operational configuration, the laser coupled to an adapter that is removably attached to the underwater vehicle, the adapter having an exit aperture for the laser that faces the marine geophysical equipment.

9. The apparatus of claim 8, further comprising:
    a targeting system coupled with the laser.

10. The apparatus of claim 9, wherein the targeting system is operable to locate the obstruction and direct the laser to illuminate the obstruction.

11. The apparatus of claim 8, wherein the marine geophysical equipment comprises a sensor streamer and the laser is operable to illuminate the obstruction while the underwater vehicle traverses a length of the sensor streamer.

12. The apparatus of claim 8, wherein the marine geophysical equipment comprises a sensor streamer and the laser is operable to illuminate a portion of the sensor streamer while the underwater vehicle traverses a length of the sensor streamer.

13. The apparatus of claim 8, wherein the marine geophysical equipment comprises a sensor streamer and the laser is operable to illuminate a portion of the sensor streamer while the apparatus traverses a length of the sensor streamer.

14. The apparatus of claim 8, wherein the laser comprises a diode laser.

15. A system for cleaning geophysical equipment, comprising:
    a cleaning vessel;
    a laser coupled with the cleaning vessel and operable to illuminate an obstruction on a geophysical marine equipment deployed in an operational configuration; and
    a targeting system coupled with the laser, wherein the laser is coupled to an adapter that is removably attached to an underwater vehicle, the adapter having an exit aperture for the laser that faces the marine geophysical equipment.

16. The system of claim 15, further comprising:
    a deployment vessel for the cleaning vessel.

17. The system of claim 16, wherein the marine geophysical equipment comprises a sensor streamer, the operational configuration comprises the sensor streamer being towed behind a survey vessel, and the laser is operable to illuminate the obstruction while the cleaning vessel traverses a length of the sensor streamer.

18. The system of claim 16, wherein the marine geophysical equipment comprises a sensor streamer and the laser is operable to illuminate a portion of the sensor streamer while the cleaning vessel traverses a length of the sensor streamer.

19. The system of claim 15, further comprising:
a streamer cleaning unit coupled with the cleaning vessel.

20. The system of claim 19, wherein the marine geophysical equipment comprises a sensor streamer and the laser is operable to illuminate a portion of the sensor streamer while the cleaning vessel traverses a length of the sensor streamer.

21. The system of claim 15, wherein the targeting system is operable to locate the obstruction and direct the laser to illuminate the obstruction.

\* \* \* \* \*